United States Patent [19]

Yamamoto et al.

[11] Patent Number: 4,687,769

[45] Date of Patent: Aug. 18, 1987

[54] 3-(3,3,3-TRIFLUOROPROPENYL) CEPHALOSPORINS

[75] Inventors: Yuichi Yamamoto, Yokohama; Takashi Yoshida; Shunzo Fukatsu, both of Tokyo; Toshiyasu Ishimaru, Kawanishi, all of Japan

[73] Assignee: Meiji Seika Kaisha, Ltd., Tokyo, Japan

[21] Appl. No.: 809,168

[22] Filed: Dec. 16, 1985

[30] Foreign Application Priority Data

Dec. 20, 1984 [JP] Japan ................... 59-267382

[51] Int. Cl.[4] ................ A61K 31/545; C07D 501/28
[52] U.S. Cl. ..................... 514/202; 540/222
[58] Field of Search .................... 544/22; 514/202

[56] References Cited

U.S. PATENT DOCUMENTS 4,255,423  3/1981  Beattie et al. ............... 424/246
4,486,586 12/1984  Narita et al. ................ 544/22
4,622,393 11/1986  Farge ........................ 540/215
4,631,274 12/1986  Takaya ...................... 514/202

Primary Examiner—Donald G. Daus
Assistant Examiner—B. Cassatt
Attorney, Agent, or Firm—Larson and Taylor

[57]  ABSTRACT

A class of new cephem compounds is now provided, which is useful as antibacterial agent and is represented by the general formula (I)

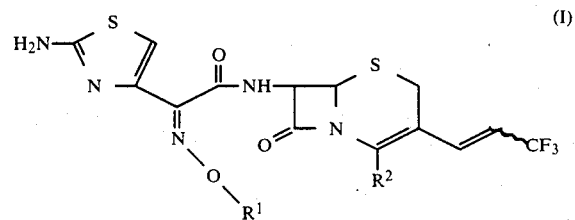

wherein $R^1$ is methyl group or carboxymethyl group and $R^2$ is carboxyl group or a protected carboxyl group, and a pharmaceutically acceptable salt or ester thereof.

11 Claims, No Drawings

3-(3,3,3-TRIFLUOROPROPENYL) CEPHALOSPORINS

SUMMARY OF THE INVENTION

This invention relates to a new cephem compound and a pharmaceutically acceptable salt or ester thereof, which are useful as antibacterial agent. More particularly, this invention relates to a new cephem compound which bears a 2-(substituted imino)-2-(2-aminothiazolyl-)acetamido group as the side chain at the 7-position of the cephem nucleus and a β-substituted vinyl group such as 3,3,3-trifluoropropenyl as the side chain at the 3-position of the cephem nucleus. This invention also relates to a pharmaceutical composition comprising the new cephem compound as active ingredient. This invention further relates to a process for the production of the new cephem compound.

BACKGROUND OF THE INVENTION

A number of cephem compounds belonging to a class of 3-substituted- or unsubstituted-3-cephem-4-carboxylic acids which have a 2-(2-amino-thiazol-4-yl)-2-(substituted or unsubstituted-alkoxyimino)-acetamido group at the 7 position of the cephem nucleus are known. These cephem compounds of this class have high antibacterial activity against Gram-negative bacteria as well as their resistant strains, but they disadvantageously exhibit rather poor antibacterial effects against Gram-positive microorganisms, as described e.g. in the "Antimicrobial Agents and Chemotherapy", 25, 98 (1984).

Besides, these cephem compounds of this class can poorly be absorbed through the digestive tubes when orally administered, and therefore these cephem compounds have been administered exclusively by injection in practice. Accordingly, many efforts have been made to provide new cephem compounds of this class which can exhibit improved absorption or uptake by the digestive tubes upon oral administration.

We, the present inventors, have extensively made our researches to overcome the above drawback of the known cephem compounds of the class as mentioned above. In the course of our researches, we have synthesized a lot of cephem compounds having different 3-substituents, and examined the antibacterial activity and the absorption through the digestive tubes of said 3-substituted cephem compounds as synthetized by us. As a result, we have now found that a class of new cephem compounds (syn-isomer) represented by the formula (I)

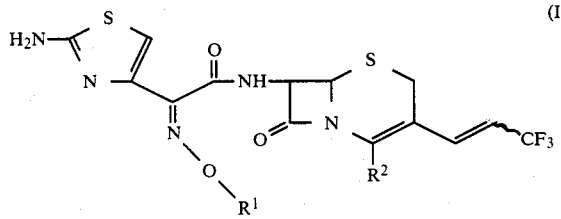

wherein R¹ is methyl group or carboxymethyl group and R² is carboxyl group or a protected carboxy group, have high antibacterial activity not only against Gram-negative bacteria and their resistant strains, but also against Gram-positive bacteria, and that these new cephem compounds can easily be absorbed or uptaken through the digestive tubes when orally administered.

DETAILED DESCRIPTION OF THE INVENTION

According to the first aspect of this invention, therefore, there is provided a cephem compound of the general formula (I) as defined above, and a pharmaceutically acceptable salt or ester thereof.

The new cephem compound of the formula (I) according to this invention includes two isomers, namely the trans-isomer and cis-isomer, depending on the relative positions of the substituent (the trifluoromethyl group-CF₃) and the hydrogen atom which are attached to the vinylic double bond of the β-substituted vinyl group at the 3-position of the cephem nucleus. The cephem compound of this invention, therefore, covers the cis-isomer, the trans-isomer and a mixture thereof.

Preferred examples of the new cephem compound of the formula (I) according to this invention are listed below;

(A)  7-[2-methoxyimino-2-(2-aminothiazol-4-yl)acetamido]-3-(3,3,3-trifluoropropenyl)-3-cephem-4-carboxylic acid (syn-isomer, cis-isomer) and its sodium salt.

(B)  7-[2-methoxyimino-2-(2-aminothiazol-4-yl)acetamido]-3-(3,3,3-trifluoropropenyl)-3-cephem-4-carboxylic acid (syn-isomer, trans-isomer) and its sodium salt.

(C)  7-[2-(carboxymethoxyimino)-2-(2-aminothiazol-4-yl)acetamido]-3-(3,3,3-trifluoropropenyl)-3-cephem-4-carboxylic acid (syn-isomer, cis-isomer).

(D)  7-[2-(carboxymethyimino)-2-(2-aminothiazol-4-yl)acetamido]-3-(3,3,3-trifluoropropenyl)-3-cephem-4-carboxylic acid (syn-isomer, trans-isomer).

(E)  7-[2-methoxyimino-2-(2-aminothiazol-4-yl)acetamido]-3-(3,3,3-trifluoropropenyl)-3-cephem-4-carboxylic acid pivaloyloxymethyl ester (syn-isomer, cis-isomer) and its hydrochloride.

(F)  7-[2-methoxyimino-2-(2-aminothiazol-4-yl)acetamido]-3-(3,3,3-trifluoropropenyl)-3-cephem-4-carboxylic acid pivaloyloxymethyl ester (syn-isomer, trans-isomer) and its hydrochloride.

(G)  7-[2-(carboxymethoxyimino)-2-(2-aminothiazol-4-yl)acetamido]-3-(3,3,3-trifluoropropenyl)-3-cephem-4-carboxylic acid pivaloyloxymethyl ester (syn-isomer, cis-isomer) and its hydrochloride.

(H)  7-[2-carboxymethoxyimino)-2-(2-aminothiazol-4-yl)acetoamido]-3-(3,3,3-trifluoropropenyl)-3-cephem-4-carboxylic acid pivaloyloxymethyl ester (syn-isomer, trans-isomer) and its hydrochloride.

(I)  7-[2-methoxyimino-2-(2-aminothiazol-4-yl)acetamido]-3-(3,3,3-trifluoropropenyl)-3-cephem-4-carboxylic acid 1-(ethoxycarbonyloxy)ethyl ester (syn-isomer, cis-isomer) and its hydrochloride.

(J)  7-[2-methoxyimino-2-(2-aminothiazol-4-yl)acetamido]-3-(3,3,3-trifluoropropenyl)-3-cephem-4-carboxylic acid 1-(ethoxycarbonyloxy)ethyl ester (syn-isomer, trans-isomer) and its hydrochloride.

(K)  7-[2-(carboxymethoxyimino)-2-(2-aminothiazol-4-yl)acetamido]-3-(3,3,3-trifluoropropenyl)-3-cephem-4-carboxylic acid 1-(ethoxycarbonyloxy)ethyl ester (syn-isomer, cis-isomer) and its hydrochloride.

(L)  7-[2-(carboxymethoxyimino)-2-(2-aminothiazol-4-yl)acetoamido]-3-(3,3,3-trifluoropropenyl)-3-cephem-4-carboxylic acid 1-(ethoxycarbonyloxy)ethyl ester (syn-isomer, trans-isomer) and its hydrochloride.

(M) 7-[2-methoxyimino-2-(2-aminothiazol-4-yl)acetamido]-3-(3,3,3-trifluoropropenyl)-3-cephem-4-carboxylic acid (5-methyl-2-oxo-1,3-dioxolen-4-yl)methyl ester (syn isomer, cis-isomer) and its hydrochloride.

(N) 7-[2-methoxyimino-2-(2-aminothiazol-4-yl)acetamido]-3-(3,3,3-trifluoropropenyl)-3-cephem-4-carboxylic acid (5-methyl-2-oxo-1,3-dioxolen-4-yl)methyl ester (syn-isomer, trans-isomer) and its hydrochloride.

(O) 7-[2-(carboxymethoxyimino)-2-(2-aminothiazol-4-yl)acetamido]-3-(3,3,3-trifluoropropenyl)-3-cephem-4-carboxylic acid (5-methyl-2-oxo-1,3-dioxolen-4-yl)methyl ester (syn-isomer, cis-isomer) and the hydrochloride.

(P) 7-[2-(carboxymethoxyimino)-2-(2-aminothiazol-4-yl)acetamido]-3-(3,3,3-trifluoropropenyl)-3-cephem-4-carboxylic acid (5-methyl-2-oxo-1,3-dioxolen-4-yl)methyl ester (syn-isomer, trans-isomer) and its hydrochloride.

The new cephem compound of the formula (I) according to this invention may be prepared by a process comprising reacting a 7-aminocephalosporanic acid derivative of the formula (II)

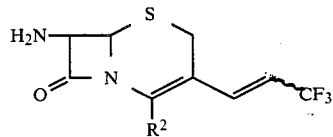 (II)

wherein $R^2$ is as defined above, with a 2-(2-aminothiazol-4-yl)-2-(alkoxyimino)acetic acid compound of the formula (III)

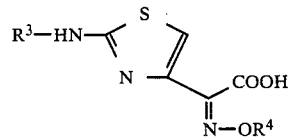 (III)

wherein $R^3$ is a hydrogen atom or an amino-protecting group and $R^4$ is methyl group or a protected carboxymethyl group, or with a carboxyl-reactive derivative of the compound of the formula (III) above, to produce a compound of the formula (IV);

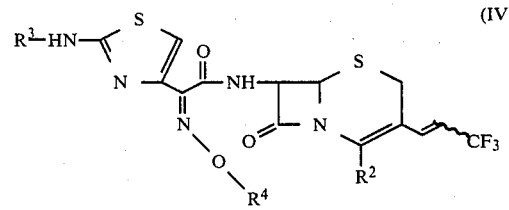 (IV)

wherein $R^2$, $R^3$ and $R^4$ are defined above, and then, if desired, removing in a known manner the remaining amino-protecting group ($R^3$) and/or the remaining carboxyl-protecting group present in the protected carboxymethyl group ($R^4$) from the compound of the formula (IV), to give the desired cephem compound of the formula (I).

Suitable examples of the aforesaid carboxyl-reactive derivative, that is to say, such a reactive derivative made reactive at the carboxyl group of the compound (III) include an acid halide, an acid anhydride, a mixed acid anhydride and an activated ester as derived from the compound of the formula (III). The amino-protecting group which may be meant by the group $R^3$ may be any known one, if it is such an amino-protecting group which is easily removable under mild reaction conditions to recover the free amino group, and the available amino-protecting group may, for example, be 2,2,2-trichloroethoxycarbonyl, chloroacetyl, t-butoxycarbonyl group and the like. Suitable examples of the carboxyl-protecting group which is present in the protected carboxymethyl group ($R^4$) may be an ester-forming group such as allyl, 2,2,2-trichloroethyl, diphenylmethyl and t-butyl groups. These amino-protecting and carboxyl-protecting groups may be selected properly according to the nature of the compound (III) to be protected.

The amino-protecting group and the carboxyl-protecting group can be removed from the condensation product of the formula (IV) according to a conventional deprotecting technique, for example, by hydrolysis or reduction. After the completion of the reaction for the synthesis of the compound of the formula (I), the product compound (I) may be purified chromatographically in a conventional manner to give a purified product of the compound (I).

According to the second aspect of this invention, there is provided a process for the production of a cephem compound of the general formula (I)

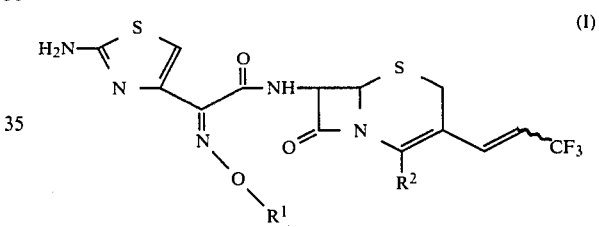 (I)

wherein $R^1$ is methyl group or carboxymethyl group and $R^2$ is carboxyl group or a protected carboxyl group, which comprises reacting a compound of the formula (II)

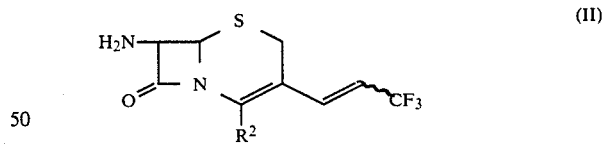 (II)

wherein $R^2$ is as defined above, or a functional equivalent thereof, with a 2-(2-amino-thiazol-4-yl)-2-alkoxyiminoacetic acid compound of the formula (III):

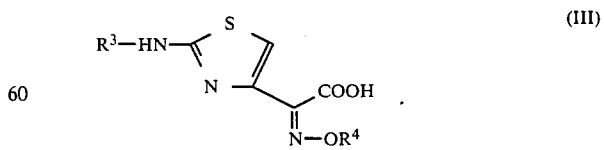 (III)

wherein $R^3$ is a hydrogen atom or an amino-protecting group and $R^4$ is a methyl group or a protected carboxymethyl group, or a carboxyl-reactive derivative thereof in an unreactive solvent to produce the compound of the formula (IV)

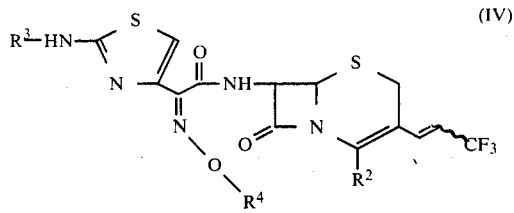

wherein $R^2$, $R^3$ and $R^4$ are as defined above, and if desired, removing the remaining amino-protecting group ($R^3$) and/or the remaining carboxyl-protecting group present in the protected carboxymethyl group ($R^4$) from the compound of the formula (IV) to produce the compound of the formula (I).

In the present process, the reaction of acylating the 7-amino group of the compound (II) with the compound (III) may usually be conducted in a conventional unreactive solvent such as water, acetone, dioxane, acetonitrile, chloroform, methylene chloride, ethylene chloride, tetrahydrofurane, ethyl acetate, N,N-dimethylformamide, pyridine, or in any other solvent which exerts no adverse effect on the progress of this reaction. These solvents may be used as a mixture with water.

In the case where the compound (III) is used in the form of a free acid or in the form of a salt, the reaction may preferably be conducted in the presence of a condensing agent. Examples of such a condensing agent may be N,N'-dicyclohexylcarbodiimide; N-cyclohexyl-N'-morpholino-ethylcarbodiimide; N-cyclohexyl-N'-(4-diethylaminocyclohexyl)carbodiimide; N,N'-diethylcarbodiimide; N,N'-diisopropylcarbodiimide; N-ethyl-N'-(3-dimethylaminopropyl)carbodiimide; N,N'-carbonyl-bis(2-methylimidazole); pentamethyleneketene-N-cyclohexylimine; diphenylketene-N-cyclohexylimine; ethoxyacetylene; 1-alkoxy-1-chloroethylene; phosphorous acid trialkylester; ethyl polyphosphate; isopropyl polyphosphate; phosphorus oxychloride; phosphorus trichloride; thionyl chloride; oxalyl chloride; triphenylphosphine; 2-ethyl-7-hydroxybenzoisoxazolium salt; 2-ethyl-5-(m-sulfophenyl)isoxazolium hydroxide (intramolecular salt); 1-(p-chlorobenzenesulfonyloxy)-6-chloro-1H-benzotriazole; Vilsmeier reagent as prepared from reaction of dimethylformamide with thionyl chloride, phosgene and phosphorus oxychloride.

This reaction according to the present process may also be conducted in the presence of an inorganic or organic base. Examples of these inorganic and organic bases may be an alkali metal hydrogen carbonate such as sodium hydrogen carbonate or potassium hydrogen carbonate, an alkali metal carbonate such as sodium carbonate or potassium carbonate, an alkaline earth metal carbonate such as calcium carbonate, a tri-(lower)alkyl amine such as trimethylamine or triethylamine, pyridine, N-(lower)alkylmorpholine, N,N-di(lower)alkylbenzylamine.

The reaction as above may be carried out at any optional temperature, and may usually be conducted under cooling or under heating.

The compound of the formula (IV) which has been prepared by the above reactions for the preparation thereof, if desired, may then be subjected to further conventional step(s) for removal of the remaining carboxyl-protecting group and/or the remaining amino-protecting group therefrom, and/or to further conventional step(s) for converting the carboxyl group(s) of the product compound (I) into a metabolically unstable, non-toxic ester (carboxylate) group. The method for removal of the carboxyl-protecting group and/or the amino-protecting group may properly be chosen according to the nature of the protecting groups to be removed.

The amino-protecting group may be removed from the product compound (IV) by a conventional deprotecting technique, for example, by hydrolysis or reduction, and for such a compound (IV) bearing an acyl group as the amino-protecting group to be removed, it is feasible to subject such compound (IV) to a reaction with an imino-halogenating agent and then with an imino-etherifing agent, if necessary, followed by hydrolysis. Acid hydrolysis is one of the conventional methods for removing the amino-protecting groups and is applicable to the removal of such groups as an alkoxycarbonyl group, formyl group and trityl group. The acids available for this acid hydrolysis may be formic acid, trifluoroacetic acid, p-toluenesulfonic acid, hydrochloric acid and other organic or inorganic acids, and preferably the acids are formic acid, trifluoroacetic acid and hydrochloric acid which afford easy after-treatment of the reaction mixture. These acids for hydrolysis are selected properly according to the nature of the amino-protecting group to be removed. This hydrolysis reaction may be carried out either in the absence of any solvent or in the presence of a solvent such as water, a hydrophilic organic solvent or a mixture of organic solvents. When trifluoroacetic acid is employed for the acid hydrolysis, the reaction may suitably be conducted in the presence of anisole.

The carboxyl-protecting group may be removed also in a conventional manner, for example, by hydrolysis or reduction. Acid hydrolysis is one of the conventional deprotection methods which is advantageously applicable to the removal of the carboxyl-protecting group of such kind as silyl group and diphenylmethyl group.

With the product compound of the formula (I), the conversion of the carboxyl group into the metabolically unstable ester group may be performed by a conventional method comprising reacting a metal salt of the corresponding carboxylic acid compound (I) with an alkyl halide such as a pivaloyloxymethyl halide e.g. chloride or a corresponding alcohol in an organic solvent.

The starting compounds of the formula (II) employed for the production of the new cephem compound (I) of this invention may be prepared by a method comprising the following two steps:

Step 1

In this Step 1, a 3-triphenylphosphoranylidenemethyl-7-protected-amino-3-cephem-4-carboxylic acid compound of the formula (V):

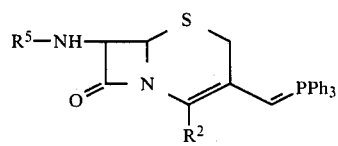

wherein $R^2$ is as defined above and $R^5$ is a known amino-protecting group is reacted with trifluoroacetaldehyde, namely the compound of the formula (VI);

$$CF_3CHO \qquad\qquad (VI)$$

to produce a compound of the formula (VII);

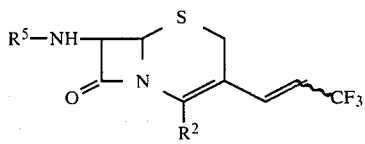

wherein $R^2$ and $R^5$ are as defined above.

The starting compound of the formula (V) includes known compounds as disclosed, for example, in the "Recent Advances in the Chemistry of β-lactam Antibiotics", page 153, and they may easily be synthesized from 7-aminocephalosporanic acid or penicillins. The compound of the formula (VI) may be used in excess over or in an equimolar proportion to the compound of the formula (V). It is preferred in practice that the compound of the formula (VI) should be charged in a slight excess to ensure smooth progress of the reaction.

The reaction of the compound (V) with the compound (VI) may usually be conducted in any solvent in which both the compounds are soluble and which exerts no adverse effect on the progress of this reaction. This reaction may be carried out at any optional temperature and may preferably be effected at ambient temperature. After the completion of this reaction, the product (VII) may, if desired, be purified in a conventional manner for purification, for example, by silica gel chromatography, isolating the desired compound of the formula (VII). The compound (VII) thus obtained is normally mixed products which comprise two isomers, namely the cis-isomer and the trans-isomer. The compound (VII) including the cis- and trans-isomers may directly be used as such in the next Step 2, or the individual isomers may be isolated separately from the compound (VII) before they are used in the next Step 2 for the preparation of the starting compound (II).

Step 2

In this Step 2, the resulting compound of the formula (VII)

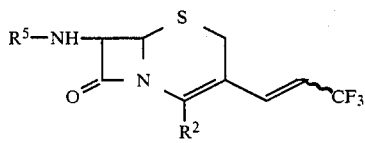

wherein $R^2$ and $R^5$ are as defined above, is subjected to a conventional deprotecting technique, for example, by hydrolysis or hydrogenolysis, for removal of the amino-protecting group from the 7-amino group, whereby a compound of the formula (II):

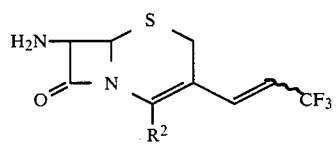

wherein $R^2$ is as defined above or a salt thereof is obtained.

Preferred examples of the salts of the compound (II) include a hydrochloride and p-toluenesulfonate of the compound (II). The method for removal of the amino-protecting group ($R^5$) may properly be chosen according to the nature of said amino-protecting group to be removed. The compound of the formula (II) obtained may be used without being isolated but may, if desired, be purified in a known manner before it is used for the production of the new cephem compound (I) of this invention.

The cephem compounds (I) of this invention and the salts or ester thereof are all novel compounds which are useful as antibacterial agent. To illustrate the utility of the new compound of this invention, we have determined and show below the minimum inhibitory concentrations of some representative examples of the new cephem compounds of this invention against growth of various bacteria in Table 1.

Referring to Table 1 below, the test compounds are identified as follows:

Compound (A): 7-[2-methoxyimino-2-(2-aminothiazol-4-yl)acetamido]-3-(3,3,3-trifluorophenyl)-3-cephem-4-carboxylic acid (syn-isomer, cis-isomer)

Compound (B): 7-[2-methoxyimino-2-(2-aminothiazol-4-yl)acetamido]-3-(3,3,3-trifluoropropenyl)-3-cephem-4-carboxylic acid (syn-isomer, trans-isomer)

TABLE 1

| | Minimum inhibitory concentrations (MIC) (μg/ml) | |
|---|---|---|
| Test microorganisms | Compound (A) | Compound (B) |
| Staphylococcus aureus 209P JC-1 | 0.20 | 0.39 |
| Staphylococcus aureus Smith | 0.39 | 0.78 |
| Escherichia coli NIHJ JC-2 | 0.78 | 0.39 |
| Klebsiella pneumoniae PCI-602 | 0.39 | 0.39 |
| Proteus mirabilis GN-79 | 0.39 | 0.39 |
| Proteus vulgaris GN-76 | 0.20 | 0.20 |
| Proteus rettgeri GN-624 | 3.13 | 1.56 |
| Salmonella typhimurium LT-2 | 0.39 | 0.20 |
| Serratia marcescens No. 1 | 0.20 | 0.39 |
| Pseudomonas cepacia M-0527 | 6.25 | 6.25 |

The new cephem compound of the formula (I) according to this invention, or a pharmaceutically acceptable salt or ester thereof may be formulated into a pharmaceutical composition by mixing with a pharmaceutically acceptable solid or liquid carrier when it is to be administered to man for the therapeutic treatment of bacterial infections.

According to a further aspect of this invention, therefore, there is provided a pharmaceutical, antibacterial composition which comprises an antibacterially effective amount of the cephem compound of the formula (I) as defined hereinbefore or a pharmaceutically acceptable salt or ester thereof as the active ingredient, in combination of a pharmaceutically acceptable carrier for the active ingredient.

The pharmaceutically acceptable carrier as mixed with the active ingredient compound may be an ordinary solid or liquid one, either organic or inorganic, which may be chosen appropriately depending on whether the pharmaceutical formulation as prepared is to be administered orally or non-orally or externally. The pharmaceutical composition of this invention may be of any conventional formulation such as capsules, tablets, sugar-coated pills, ointment, suppository, solution, suspension and emulsion. Other conventional additives, including stabilizing agent, wetting agent, emulsifying agent, flavoring agent, colorant may also be incorporated into the pharmaceutical composition of this invention containing the cephem compound of the formula (I) as the active ingredient.

This invention is now illustrated with reference to the following Examples. Example 1 illustrates the procedure for preparing one of the starting compounds (II) available for the production of the new cephem compounds (I) of this invention.

EXAMPLE 1

Production of 7-(phenylacetamido)-3-(3,3,3-trifluoropropenyl)-3-cephem-4-carboxylic acid diphenylmethyl ester of the formula:

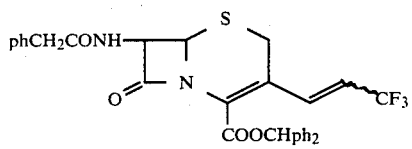

where ph denotes a phenyl group.

3-Triphenylphosphoranylidenemethyl-7-phenylacetamido-3-cephem-4-carboxylic acid diphenylmethyl ester (7.59 g) of the formula

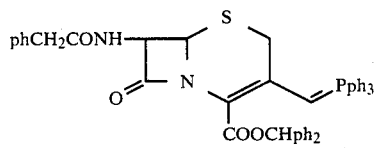

was suspended in methylene chloride (80 ml), to which a solution of trifluoroacetaldehyde (3 g) in methylene chloride (20 ml) was added at once under ice-cooling. The resultant mixture was stirred for 30 minutes at ambient temperature. The reaction mixture obtained was then concentrated under reduced pressure. The concentrated residue was purified chromatographically on a column of silica gel (20 g). The eluate fractions containing the titled compound were combined together and concentrated to dryness under reduced pressure. Crystallization of the residue from n-hexane gave the titled compound as a pure crystalline product. Yield 4 g (69%). According to NMR. spectrum, it was revealed that the crystalline product obtained was a mixture containing the cis-isomer and trans-isomer at a molar ratio of about 6:4.

m.p. 128°–148° C. IR (Nujol): 3300, 1780, 1720, 1690, 1650 cm$^{-1}$; NMR (CDCl$_3$).(360 MHz): 3.40 (AB, J=18.2 Hz, 2-Proton of the cis-isomer), 3.49 (s, 2-proton of the trans-isomer), 3.65 (AB, J=16.1 Hz, ph CH$_2$CO), 4.99 (d, J=5.0 Hz, 6-Proton), 5.00 (d, J=5.0 Hz, 6-Proton), 5.55 (d-q, J=8.2 Hz, 12.3 Hz,

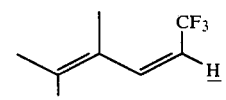

5.80 (d-q, J=6.4 Hz, 16.3 Hz,

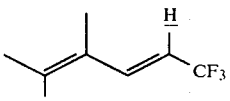

5.90 (m, 7-Proton), 6.68 (d, J=13.3 Hz, —CONH—), 6.86 (s, —COOCHph$_2$), 7.01 (s, —COOCHph$_2$), 7.26–7.41 (m, Ar).

EXAMPLE 2

(a) Production of 7-[2-methoxyimino-2-(2-chloroacetamidothiazol-4-yl)]-acetamido-3-(3,3,3-trifluoropropenyl)-3-cephem-4-carboxylic acid diphenylmethyl ester of the formula

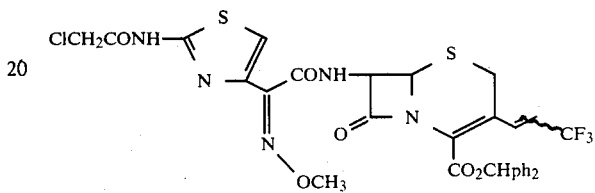

The compound (4 g) as obtained in the Example 1 above was dissolved in methylene chloride (60 ml), to which were then added phosphorus pentachloride (1.91 g) and dimethylaniline (2.6 ml) at −20° C. The resultant mixture was stirred for 2 hours under ice-cooling and then was admixed at once with methanol (5.6 ml) at −20° C., followed by stirring the mixture for 2 hours under ice-cooling. The resulting reaction mixture was mixed with ice-water (20 ml) and stirred vigorously for 10 minutes under ice-cooling. The reaction mixture was allowed to stand until it separated into the aqueous phase and the organic solvent phase. The organic solvent phase was separated from the aqueous phase. The organic solvent phase was washed successively with water and then with aqueous sodium hydrogen carbonate and dried over an hydrous magnesium sulfate. The magnesium sulfate was removed from the organic phase by filtration, and the filtrate (the organic phase) was concentrated under reduced pressure to a volume of about 40 ml. The resulting concentrate containing therein 7-amino-3-(3,3,3-trifluoropropenyl)-3-cephem-4-carboxylic acid diphenylmethyl ester as formed was mixed with 2-methoxyimino-2-[2-chloroacetamidothiazol-4-yl)acetic acid (1.92 g) and pyridine (1.7 ml), and to the resultant mixture was further added phosphorus oxychloride (1.06 g) at −20° C. After 30 minutes, the reaction mixture obtained was mixed with ice-water and stirred vigorously. The whole mixture was allowed to stand until it separated into the aqueous phase and the organic solvent phase. The organic solvent phase was removed from the aqueous phase, and washed successively with aqueous 1N HCl, with aqueous sodium hydrogen carbonate and with aqueous sodium chloride. The organic solvent phase thus treated was then dried over anhydrous magnesium sulfate and concentrated under reduced pressure, affording to deep-violet-colored oil. This oil was purified by dissolving this oil in benzene (10 ml) and chromatographing the resulting solution on a column of silica gel (Wako Gel C-300, a product of Wako Pure Chemical Ind. Ltd., Japan; 200 g) as developed with benzene-ethyl acetate (2:1), to afford 1.82 g of the cis-isomer and 1.17 g of the trans-isomer of the titled compound, respectively as colorless solids.

NMR (90 MHz, CDCl₃): Cis-isomer: 3.47 (2H, AB, J=18 Hz), 4.08 (3H, s), 4.15 (2H, s), 5.15 (1H, d, J=5.1 Hz), 5.57 (1H, d-q, J=12.1 Hz, 7.9 Hz), 6.01 (1H, d-d, J=5.1 Hz, 9.0 Hz), 6.73 (1H, br-d, J=12.1 Hz), 6.89 (1H, s), 7.20–7.40 (m, Ar). Trans-isomer:3.57 (2H, s), 4.09 (3H, s), 4.19 (2H, s), 5.15 (1H, d, J=5.1 Hz), 5.85 (1H, d-q, J=16.3 Hz, 6.4 Hz), 6.03 (1H, d-d, J=5.1 Hz, 8.8 Hz), 7.03 (1H, s), 7.20–7.40 (m).

(b) Production of 7-[2-methoxyimino-2-(2-amino-thiazol-4-yl)acetamido]-3-(3,3,3-trifluoropropenyl)-3-cephem-4-carboxylic acid (cis-isomer) sodium salt of the formula

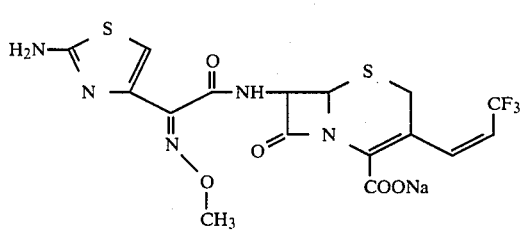

The compound (the cis-isomer) (400 mg) as obtained in the Example 2(a) above was dissolved in N,N-dimethylacetamide (1 ml), to which thiourea (85 mg) was then added. The mixture obtained was stirred for 4 hours at ambient temperature to effect the reaction for removal of the amino-protecting group. The reaction mixture was mixed with ethyl acetate and a dilute aqueous sodium hydrogen carbonate. The whole mixture was then allowed to stand until it separated into the aqueous phase and the organic solvent phase. The organic solvent phase was removed from the aqueous phase, washed with aqueous sodium chloride, dried over anhydrous magnesium sulfate and concentrated to dryness. To the solid residue obtained were added anisole (0.5 ml) and trifluoroacetic acid (4 ml). The mixture obtained was allowed to stand for 1 hour at ambient temperature. The mixture was then concentrated under reduced pressure, and the residue was admixed with diisopropyl ether (10 ml) and hexane (5 ml). The solid material as formed was removed from the liquid phase by filtration and suspended in cold water (3 ml), to which was then added aqueous sodium hydrogen carbonate until the solid material was dissolved therein with formation of the sodium salt of the titled compound. The resultant solution was passed through a column of 20 ml of a non-ionic, microporous resin, Diaion HP-20 (a product of Mitsubishi Kasei Co., Ltd., Japan), which was then washed and eluted with water containing 30% methanol. The eluate fractions containing the desired compound were combined together and concentrated to dryness in vacuo to give 150 mg of the titled compound.

NMR (90 MHz, D₂O): 3.54 (2H, AB, J=18 Hz), 3.99 (3H, s), 5.27 (1H, d, J=4.6 Hz), 5.60–6.00 (2H, m), 6.74 (1H, d, J=12.5 Hz), 7.01 (1H, s).

(c) Production of 7-[2-methoxyimino-2-(2-amino-thiazol-4-yl)acetamido]-3-(3,3,3-trifluoropropenyl)-3-cephem-4-carboxylic acid (trans-isomer) sodium salt of the formula

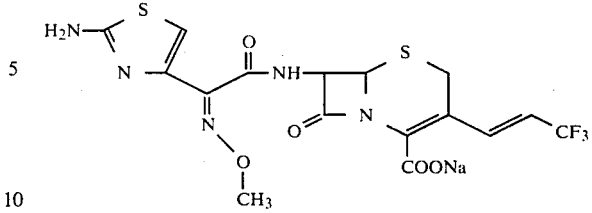

The compound (the trans-isomer) (250 mg) as obtained in the Example 2(a) was processed in the same manner as in the above step (b) to afford the titled compound in a yield of 105 mg.

NMR (D₂O): 3.65 (2H, s), 3.99 (3H, s), 5.28 (1H, d, J=4.8 Hz), 5.82 (1H, d, J=4.8 Hz), 6.00 (1H, d-q, J=7, 16 Hz), 7.02 (1H, s), 7.23 (1H, br-d, J=16 Hz).

EXAMPLE 3

(a) Production of 7-[2-(t-butoxycarbonylmethoxyimino)-2-(2-tritylaminothiazol-4-yl)acetamido]-3-(3,3,3-trifluoropropenyl)-3-cephem-4-carboxylic acid diphenylmethyl ester of the formula

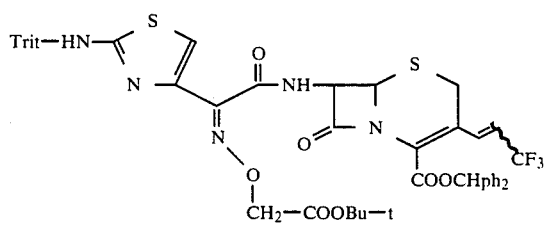

where Trit denotes trityl group, Bu-t denotes t-butyl group, and ph denotes phenyl group.

7-Phenylacetamido-3-(3,3,3-trifluoropropenyl)-3-cephem-4-carboxylic acid diphenylmethyl ester (1.5 g) as obtained in the Example 1 was processed and reacted with 2-(t-butoxycarbonyl-methoxyimino)-2-(2-tritylaminothiazol-4-yl)acetic acid and the resulting reaction product was then treated in the same manner as in the Example 2(a) above to afford a crude product of the titled compound. The crude product was purified by chromatographing a solution of said product in benzene similarly to the Example 2(a) on a column of silica gel to give 500 mg of the cis-isomer and 410 mg of the trans-isomer of the titled compound.

NMR (90 MHz, CDCl₃): Trans-isomer: 1.40 (9H, s), 3.49 (2H, s), 4.73 (2H, s), 5.07 (1H, d, J-5.0 Hz), 5.78 (1H, d-q, J=6.5 Hz, 16.2 Hz), 5.91 (1H, d-d, J=5.0 Hz, 8.6 Hz), 6.78 (1H, s), 6.99 (1H, s), 7.20–7.40 (m), 8.71 (1H, d, J=8.6 Hz). Cis-isomer: 1.40 (9H, s), 3.42 (2H, AB, J=18.5 Hz), 4.73 (2H, s), 5.05 (1H, d, J=5.0 Hz), 5.52 (1H, d-q, J=8.0 Hz, 12.2 Hz), 5.94 (1H, d-d, J=5.0 Hz, 9.0 Hz), 6.69 (1H, d, J=12.2 Hz), 6.79 (1H, s), 6.85 (1H, s), 7.20–7.40 (m), 8.64 (1H, d, J=9.0 Hz).

(b) Production of 7-[2-carboxymethoxyimino-2-(2-aminothiazol-4-yl)acetamido]-3-(3,3,3-trifluoropropenyl)-3-cephem-4-carboxylic acid (cis-isomer) of the formula

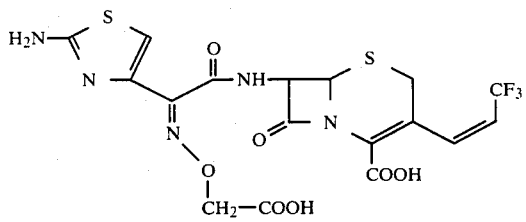

The compound (the cis-isomer) (500 mg) as obtained in the Example 3(a) above was dissolved in a mixture of anisole (0.5 ml) and trifluoroacetic acid (2 ml). The resultant solution was allowed to stand for 90 minutes at ambient temperature and then was concentrated to a small volume under reduced pressure. The resultant residue was admixed with isopropyl ether (10 ml) and hexane (10 ml), to deposit a precipitate. This precipitate was taken up into cold water, to which was added aqueous sodium hydrogen carbonate. The solution obtained was passed through a column of Diaion HP-20 (30 ml), which was eluted with water and then with 30% aqueous methanol. The eluant fractions containing the desired compound were combined together and conentrated. The concentrate was freeze-dried. The titled compound as the sodium salt was thus obtained in a yield of 165 mg.

NMR (90 MHz, D$_2$O): 3.53 (2H, AB, J=18.5 Hz), 4.56 (2H, s), 5.26 (1H, d, J=5.0 Hz), 5.81 (1H, d-q, J=8.7 Hz, 12.2 Hz), 5.84 (1H, d, J=5.0 Hz), 6.75 (1H, br-d, J=12.2 Hz), 7.02 (1H, s).

(c) Production of 7-[2-carboxymethoxyimino-2-(2-aminothiazol-4-yl)-acetamido]-3-(3,3,3-trifluoropropenyl)-3-cephem-4-carboxylic acid (trans-isomer) of the formula

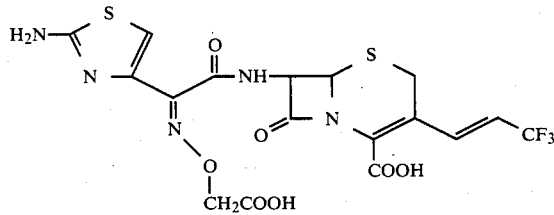

The compound (the trans-isomer) (400 mg) as obtained in the Example 3(a) above was processed in the same manner as in the Example 3(b) above, to afford 115 mg of the titled compound.

NMR (90 MHz, D$_2$O): 3.63 (2H, s), 4.54 (2H, s), 5.26 (1H, d, J=5.1 Hz), 5.82 (1H, d, J=5.1 Hz), 5.96 (1H, d-q, J=6.6 Hz, 16.5 Hz), 7.00 (1H, s), 7.20 (1H, d-q, 2.5 Hz, 16.5 Hz).

EXAMPLE 4

(a) Production of 7-phenylacetamido-3-(3,3,3-trifluoropropenyl)-3-cephem-4-carboxylic acid pivaloyloxymethyl ester of the formula

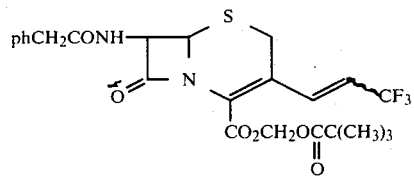

The compound (1.48 g) as obtained in the Example 1 above was dissolved in a mixture of methylene chloride (5 ml), anisole (1 ml) and trifluoroacetic acid (5 ml), and the resultant solution was allowed to stand for 15 minutes at ambient temperature. The solution was then concentrated under reduced pressure. The residue obtained was mixed with isopropyl ether (20 ml) and n-hexane (10 ml), and the precipitate as deposited was recovered by filtration. The solid so obtained was dissolved in dimethylsulfoxide (10 ml), and the resultant solution was mixed with potassium carbonate (340 mg) and iodomethyl pivalate (1.3 g), followed by stirring the mixture for 30 minutes under ice-cooling. The reaction solution obtained was mixed with ethyl acetate (50 ml), washed successively with water and with aqueous sodium chloride, and then dried over anhydrous magnesium sulfate. The dried solution was distilled to remove the solvent therefrom, and the solid residue obtained was purified by chromatographing it similarly to the Example 2(a) on a column of silica gel, to give 320 mg of the cis-isomer and 280 mg of the trans-isomer of the titled compound.

NMR (90 MHz, CDCl$_3$): Cis-isomer: 1.20 (9H, s), 3.40 (2H, AB, J=19 Hz), 3.62 (2H, s), 4.98 (1H, d, J=5.0 Hz), 5.50–5.93 (4H, m), 6.05 (1H, d, J=9 Hz), 6.71 (1H, d, J=12 Hz), 7.20–7.40 (5H, m). Trans-isomer: 1.20 (9H, s), 3.50 (2H, s), 3.62 (2H, s), 4.98 (1H, d, J=b 5 Hz), 5.65–6.0 (4H, m), 6.15 (1H, d, J=9 Hz), 7.20–7.55 (6H, m).

(b) Production of 7-[2-methoxyimino-2-(2-chloroacetamidothiazol-4-yl)-acetamido]-3-(3,3,3-trifluoropropenyl)-3-cephem-4-carboxylic acid (cis-isomer) pivaloyloxymethyl ester of the formula

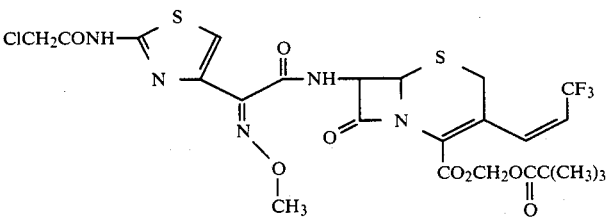

The compound (the cis-isomer) (320 mg) as obtained in the Example 4(a) above was dissolved in methylene chloride (6 ml), and to the resultant solution were added dimethylaniline (0.23 ml) and phosphorus pentachloride (170 mg) at −20° C., followed by stirring the mixture for 2 hours under ice-cooling to effect the reaction. The reaction solution was mixed with methanol (0.5 ml) at −20° C. and stirred for 3 hours under ice-cooling. The mixture obtained was then mixed with ice-water (10 ml) and stirred vigorously for 30 minutes. The mixture so treated was extracted with methylene chloride, and the extract obtained was washed with water and dried over anhydrous magnesium sulfate. The resulting concentrate containing 7-amino-3-(3,3,3-trifluoropropenyl)-3-cephem-4-carboxylic acid pivaloyloxy-methyl ester as formed was admixed with pyridine (0.2 ml) and 2-methoxyimino-2-(2-chloroacetamidothiazol-4-yl)acetic acid (170 mg), followed by cooling the resultant mixture to −20° C. The cooled mixture was mixed with phosphorus oxychloride (130 mg) and stirred for 30 minutes to effect the condensation reaction. The reaction mixture was washed well with water and dried over anhydrous magnesium sulfate. The dried reaction mixture was distilled to remove the solvent therefrom, and a deep violet-colored oil was obtained. This oil was purified chromatographically on a column of silica gel to afford 300 mg (yield 73%) of the titled compound as a colorless solid.

NMR (90 MHz, CDCl$_3$): 1.20 (9H, s), 3.50 (2H, AB, J=18 Hz), 4.07 (3H, s), 4.25 (2H, s), 5.13 (1H, d, J=5 Hz), 5.74 (1H, d-q, J=7.5 Hz, 12 Hz), 5.82 (2H, s), 6.02 (1H, d-d, J=5 Hz, 8.9 Hz), 6.76 (1H, d, J=12 Hz), 7.32 (5H, s).

(c) Production of 7-[2-methoxyimino-2-(2-aminothiazol-4-yl)-acetamido]-3-(3,3,3-trifluoropropenyl)-3-cephem-4-carboxylic acid (cis-isomer) pivaloyloxymethyl ester of the formula

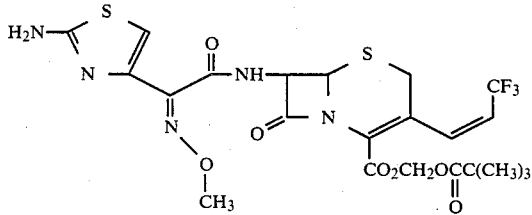

The compound (300 mg) as obtained in the Example 4(b) above was dissolved in N,N-dimethylacetamide (2 ml), to which thiourea (80 mg) was then added. After effecting the reaction for 4 hours at ambient temperature, the reaction mixture was mixed with ethyl acetate, water and aqueous sodium hydrogen carbonate.

The resultant mixture was then separated into the aqueous phase and the organic solvent phase. The organic phase was then taken, washed with aqueous sodium chloride, dried over anhydrous magnesium sulfate and distilled to remove the solvent therefrom. The solid residue obtained was purified by chromatographing a solution of said solid in ethyl acetate similarly to the Example 2(a) on a column of silica gel, to afford the titled compound (200 mg, yield 75%), as a faintly yellow-colored solid.

NMR (90 MHz, CDCl$_3$): 1.20 (9H, s), 3.47 (2H, AB, J=18 Hz), 4.01 (3H, s), 5.11 (1H, d, J=5 Hz), 5.56 (2H, br-s), 5.82 (2H, s), 5.60–5.90 (1H, m), 6.06 (1H, d-d, J=5 Hz, 9 Hz), 6.74 (1H, s), 6.76 (1H, br-d, J=12 Hz), 7.82 (1H, d, J=9 Hz).

EXAMPLE 5

(a) Production of 7-[2-methoxyimino-2-(2-chloroacetamidothiazol-4-yl)-acetamido]-3-(3,3,3-trifluoropropenyl)-3-cephem-4-carboxylic acid (trans-isomer) pivaloyloxymethyl ester of the formula

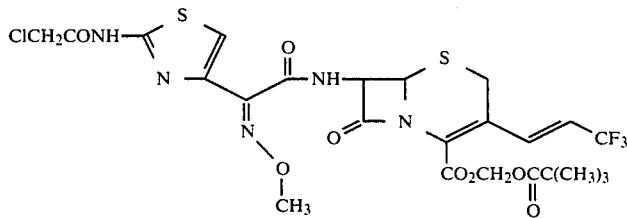

The compound (the trans-isomer) (280 mg) as obtained in the Example 4(a) above was processed and reacted with 2-methoxyimino-2-(2-chloroacetamidothiazol-4-yl)-acetic acid, followed by the treatments of the reaction mixture, in the same manner as in the procedure of the Example 4(b), to afford the titled compound (250 mg, yield 70%) as a colorless solid.

NMR (90 MHz, CDCl$_3$): 1.22 (9H, s), 3.60 (2H, s), 4.06 (3H, s), 4.25 (2H, s), 5.12 (1H, d, J=5 Hz), 5.89 (2H, s), 5.75–6.10 (2H, m), 7.30–7.58 (7H, m).

(b) Production of 7-[2-methoxyimino-2-(2-aminothiazol-4-yl)-acetamido]-3-(3,3,3-trifluoropropenyl)-3-cephem-4-carboxylic acid (trans-isomer) pivaloyloxymethyl ester of the formula

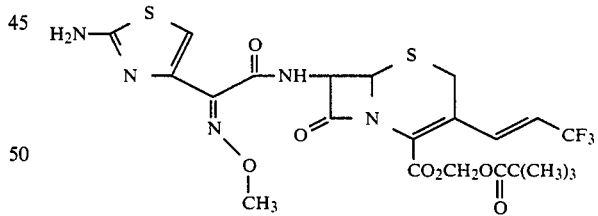

The compound (250 mg) as obtained in the Example 5(a) above was processed in the same manner as in the procedure of the Example 4(c) to afford the titled compound (150 mg, yield 68%) as a faintly cream-colored solid.

NMR (90 MHz, CDCl$_3$): 1.21 (9H, s), 3.59 (2H, s), 4.01 (3H, s), 5.12 (1H, d, J=5 Hz), 5.49 (2H, br-s), 5.90 (2H, br-s), 5.75–6.00 (1H, m), 6.05 (1H, d-d, J=5 Hz, 9 Hz), 6.78 (1H, s), 7.47 (1H, d-q, J=16 Hz, 2 Hz), 7.72 (1H, d, J=9 Hz).

EXAMPLE 6

(a) Production of 7-phenylacetamido-3-(3,3,3-trifluoropropenyl)-3-cephem-4-carboxylic acid (5-methyl-2-oxo-1,3-dioxolen-4-yl)methyl ester of the formula

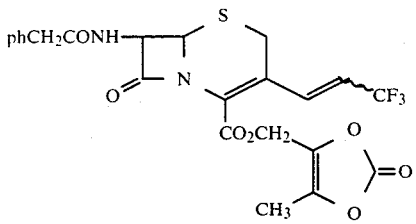

The compound (1.76 g) as obtained in the Example 1 was dissolved in a mixture of methylene chloride (6 ml), anisole (1 ml) and trifluoroacetic acid (6 ml), and the resultant solution was allowed to stand for 15 minutes at ambient temperature. The reaction mixture obtained was concentrated under reduced pressure, and the concentrated solution was mixed with isopropyl ether (20 ml) and hexane (10 ml) to deposit a precipitate. The precipitate as recovered was dissolved in aqueous ethanol containing sodium hydrogen carbonate (252 mg), and the resultant solution was concentrated to dryness under reduced pressure. The resultant solid residue comprising 7-phenylacetamido-3-(3,3,3-trifluoropropenyl)-3-cephem-4-carboxylic acid as formed was dissolved in dimethylsulfoxide (10 ml), to which 4-bromomethyl-5-methyl-2-oxo-1,3-dioxolen (870 mg) was then added. The mixture obtained was kept for 30 minutes at ambient temperature to effect the esterification reaction. The reaction solution was concentrated to dryness, and the residue was processed and purified by chromatographing similarly to the Example 2(a), to afford 500 mg of the cis-isomer and 380 mg of the trans-isomer of the titled compound.

NMR (90 MHz, CDCl$_3$): Cis-isomer: 2.14 (3H, s), 3.38 (2H, AB, J=19 Hz), 3.62 (2H, s), 4.92 (2H, AB, J=13 Hz), 4.98 (1H, d, J=5 Hz), 5.65 (1H, d-q, J=8 Hz, 13 Hz), 5.83 (1H, d-d, J=5 Hz, 9 Hz), 6.02 (1H, d, J=9 Hz), 6.65 (1H, d, J=13 Hz), 7.20–7.40 (5H, m). Trans-isomer): 2,16 (3H, s), 3.51 (2H, s), 3.63 (2H, s), 4.98 (1H, d, J=5 Hz), 5.00 (2H, AB, J=13 Hz), 5.67–6.10 (1H, m), 5.88 (1H, d-d, J=5 Hz, 9 Hz), 6.02 (1H, d, J=9 Hz), 7.20–7.50 (6H, m).

(b) Production of 7-[2-methoxyimino-2-(2-chloroacetamidothiazol-4-yl)acetamido]-3-(3,3,3-trifluoropropenyl)-3-cephem-4-carboxylic acid (cis-isomer) (5-methyl-2-oxo-1,3-dioxolen-4-yl) methyl ester of the formula

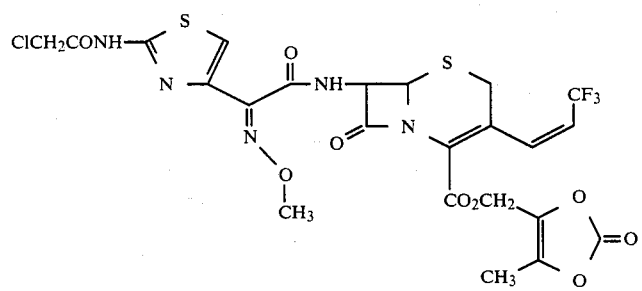

The compound (cis-isomer) (500 mg) as obtained in the Example 6(a) above was processed and reacted with 2-methoxyimino-2-(2-chloroacetamidothiazol-4-yl)-acetic acid, followed by the treatments of the reaction mixture, in the same manner as in the procedures of the Example 4(b), to give the titled compound (490 mg, yield 77%).

NMR (90 MHz, CDCl$_3$): 2.15 (3H, s), 2.49 (2H, AB, J=18 Hz), 4.06 (3H, s), 4.24 (2H, s), 4.96 (2H, AB, J=13 Hz), 5.14 (1H, d, J=5 Hz), 5.74 (1H, d-q, J=9 Hz, 13 Hz), 6.05 (1H, d-d, J=5 Hz, 9 Hz), 6.72 (1H, d, J=13 Hz), 7.22 (1H, s), 7.55 (1H, d, J=9 Hz).

(c) Production of 7-[2-methoxyimino-2-(2-aminothiazol-4-yl)-acetamido]-3-(3,3,3-trifluoropropenyl)-3-cephem-4-carboxylic acid (cis-isomer) (5-methyl-2-oxo-1,3-dioxolen-4-yl)methyl ester of the formula

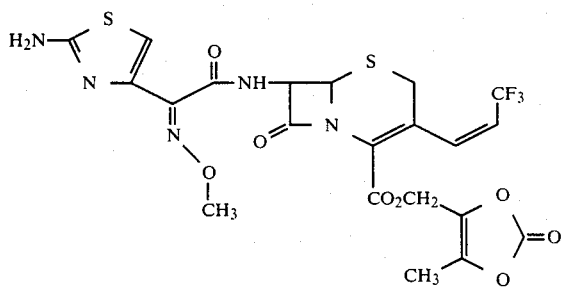

The compound (490 mg) as obtained in the Example 6(b) above was dissolved in N,N-dimethylacetamide (5 ml). The resultant solution was mixed with thiourea (112 mg) and kept for 4 hours at ambient temperature to effect the reaction for removal of the amino-protecting group. The reaction solution was then admixed with tetrahydrofuran (10 ml), ethyl acetate (20 ml) and ice-water (10 ml). The resulting mixture was then adjusted to pH 7.0 by addition of aqueous sodium hydrogen carbonate and extracted with ethyl acetate. The remaining mixture, after the separation of the ethyl acetate layer, was allowed to stand until it separated into the organic solvent phase and the aqueous phase. The organic solvent phase was separated from the aqueous phase, washed with aqueous sodium chloride and dried. The dried organic solvent phase was distilled to remove the solvent therefrom. The solid residue was purified by chromatographing similarly to the Example 2(a) on a column of silica gel, giving the titled compound (240 mg), as a fintly yellow-colored solid.

NMR (90 MHz, CDCl$_3$): 2.16 (3H, s), 3.45 (2H, AB, J=18 Hz), 4.01 (3H, s), 4.96 (2H, AB, J=15 Hz), 5.12 (1H, d, J=5 Hz), 5.44 (2H, br-s), 5.73 (1H, d-q, J=9 Hz, 13 Hz), 6.08 (1H, d-d, J=5 Hz, 9 Hz), 6.70 (1H, br-d, J=13 Hz), 6.72 (1H, s), 7.82 (1H, d, J=9 Hz).

EXAMPLE 7

(1) Production of 7-[2-methoxyimino-2-(2-chloroacetamidothiazol-4-yl)-acetamido]-3-(3,3,3-trifluoropropenyl)-3-cephem-4-carboxylic acid (trans-isomer) (5-methyl-2-oxo-1,3-dioxol-4-yl)methyl ester of the formula

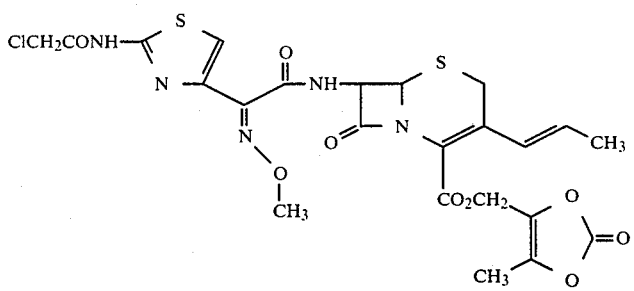

The compound (the trans-isomer) (380 mg) as obtained in the Example 6(a) was processed and reacted with 2-methoxyimino-2-(2-chloroacetamidothiazol-4-yl)-acetic acid, followed by the treatments of the reaction mixture, in the same manner as in the procedures of the Example 4(b) to afford the titled compound (390 mg, yield 80%).

NMR (9 MHz, CDCl$_3$): 2.20 (3H, s), 3.61 (2H, s) 4.05 (3H, s), 4.26 (2H, s), 5.04 (2H, AB, J=13 Hz), 5.13 (1H, d, J=5 Hz), 5.75–6.10 (1H, m), 6.02 (1H, d-d, J=5 Hz, 9 Hz), 7.27 (1H, s), 7.47 (1H, br-d, J=16 Hz), 7.56 (1H, d, J=9 Hz).

(b) Production of 7-[2-methoxyimino-2-(2-aminothiazol-4-yl)-acetamido[-3-(3,3,3-triflouoropropenyl)-3-cephem-4-carboxylic acid (trans-isomer) (5-methyl-2-oxo-1,3-dioxol-4-yl)methyl ester of the formula

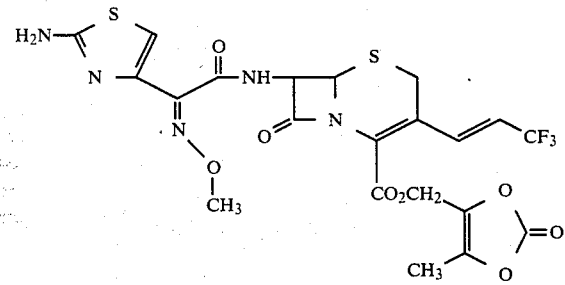

The compound (390 mg) as obtained in the Example 7(a) above was processed in the same manner as in the procedures of the Example 6(c) to afford the titled compound (120 mg).

NMR (90 MHz, CDCl$_3$): 2.20 (3H, s), 3.60 (2H, s), 4.02 (3H, s), 5.06 (2H, AB, J=14 Hz), 5.12 (1H, d, J=5 Hz), 5.50 (2H, br-s), 5.70–6.10 (1H, m), 6.07 (1H, d-d, J=5 Hz, 9 Hz), 6.71 (1H, s), 7.48 (1H, d-q, J=16 Hz, 1.5 Hz), 7.91 (1H, d, J=9 Hz).

What we claim is:

1. A cephem compound of the formula (I)

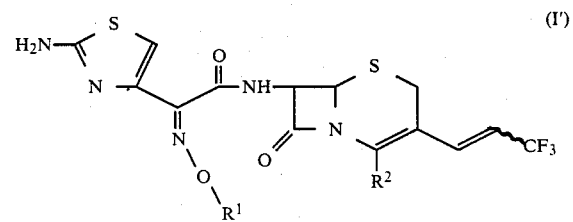

wherein R$^1$ is methyl group or carboxymethyl group and R$^2$ is carboxyl group or a carboxyl group, protected by a silyl group or by a diphenylmethyl group and a pharmaceutically acceptable salt or ester thereof.

2. A cephem compound as claimed in claim 1 which is selected from:
7-[2-methoxyimino-2-(2-aminothiazol-4-yl)acetamido]-3-(3,3,3-trifluoropropenyl)-3-cephem-4-carboxylic acid (syn-isomer, cis-isomer) and its sodium salt;
7-[2-methoxyimino-2-(2-aminothiazol-4-yl)acetamido]-3-(3,3,3-trifluoropropenyl)-3-cephem-4-carboxylic acid (syn-isomer, trans-isomer) and its sodium salt;
7-[2-(carboxymethoxyimino)-2-(2-aminothiazol-4-yl)acetamido]-3-(3,3,3-trifluoropropenyl)-3-cephem-4-carboxylic acid (syn-isomer, cis-isomer); and
7-[2-(carboxymethoxyimino)-2-(2-aminothiazol-4-yl)acetamido]-3-(3,3,3-trifluoropropenyl)-3-cephem-4-carboxylic acid (syn-isomer, trans-isomer).

3. A cephem compound as claimed in claim 1 which is selected from:
7-[2-methoxyimino-2-(2-aminothiazol-4-yl)acetamido]-3-(3,3,3-trifluoropropenyl)-3-cephem-4-carboxylic acid pivaloyloxymethyl ester (syn-isomer, cis-isomer) and its hydrochloride;
7-[2-methoxyimino-2-(2-aminothiazol-4-yl)acetamido]-3-(3,3,3-trifluoropropenyl)-3-cephem-4-carboxylic acid pivaloyloxymethyl ester (syn-isomer, trans-isomer) and its hydrochloride;
7-[2-(carboxymethoxyimino)-2-(2-aminothiazol-4-yl)acetamido]-3-(3,3,3-trifluoropropenyl)-3-cephem-4-carboxylic acid pivaloyloxymethyl ester (syn-isomer, cis-isomer) and its hydrochloride; and
7-[2-(carboxymethoxyimino)-2-(2-aminothiazol-4-yl)acetamido]-3-(3,3,3-trifluoropropenyl)-3-cephem-4-carboxylic acid pivaloyloxymethyl ester (syn-isomer, trans-isomer) and its hydrochloride.

4. A cephem compound as claimed in claim 1 which is selected from:
7-[2-methoxyimino-2-(2-aminothiazol-4-yl)acetamido]-3-(3,3,3-trifluoropropenyl)-3-cephem-4-carboxylic acid 1-(ethoxycarbonyloxy) ethyl ester (syn-isomer, cis-isomer) and its hydrochloride;
7-[2-methoxyimino-2-(2-aminothiazol-4-yl)acetamido]-3-(3,3,3-trifluoropropenyl)-3-cephem-4-carboxylic acid 1-(ethoxycarbonyloxy) ethyl ester (syn isomer, trans-isomer) and its hydrochloride; 7-[2-(carboxymethoxyimino)-2-(2-aminothiazol-4-yl)acetamido]-3-(3,3,3-trifluoropropenyl)-3-cephem-4-carboxylic acid 1-(ethoxycarbonyloxy) ethyl ester (syn-isomer, cis-isomer) and its hydrochloride; and
7-[2-(carboxymethoxyimino)-2-(2-aminothiazol-4-yl)acetamido]-3-(3,3,3-trifluoropropenyl)-3-cephem-4-carboxylic acid 1-(ethoxycarbonyloxy) ethyl ester (syn-isomer, trans-isomer) and its hydrochloride.

5. A cephem compound as claimed in claim 1 which is selected from:
7-[2-methoxyimino-2-(2-aminothiazol-4-yl) acetamido]-3-(3,3,3-trifluoropropenyl)-3-cephem-4-carboxylic acid (5-methyl-2-oxo-1,3-dioxolen-4-yl)methyl ester (syn-isomer, cis-isomer) and its hydrochloride;
7-[2-methylimino-2-(2-aminothiazol-4-yl) acetamido]-B 3-(3,3,3-trifluoropropenyl)-3-cephem-4-carboxylic acid (5-methyl-2-oxo-1,3-dioxolen-4-yl)methyl ester (syn-isomer, trans-isomer) and its hydrochloride;
7-[2-(carboxymethoxyimino)-2-(2-aminothiazol-4-yl)acetamido]-3-(3,3,3-trifluoropropenyl)-3-cephem-4-carboxylic acid (5-methyl-2-oxo-1,3-dioxolen-4-yl)methyl ester (syn-isomer, cis-isomer) and its hydrochloride; and
7-[2-carboxymethoxyimino-2-(2-aminothiazol-4-yl) acetamido]-3-(3,3,3-trifluoropropenyl)-3-cephem-4-carboxylic acid (5-methyl-2-oxo-1,3-dioxolen-4-yl)methyl ester (syn-isomer, trans-isomer) and its hydrochloride.

6. A cephem compound of the formula

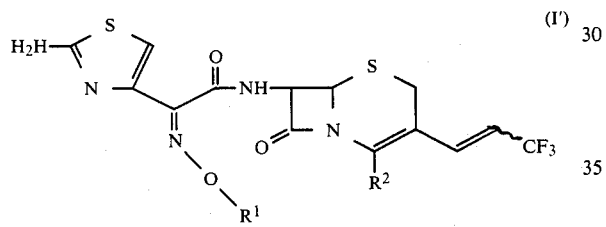

wherein $R^1$ is methyl group and $R^2$ is carboxyl group or a silyl- or diphenylmethyl-protected carboxyl group, and a pharmaceutically acceptable salt or ester thereof.

7. A cephem compound which is selected from:
7-[2-methoxyimino-2-(2-aminothiazol-4-yl)acetamido]-3-(3,3,3-trifluoropropenyl)-3-cephem-4-carboxylic acid (syn-isomer, cis-isomer) and its sodium salt;
7-[2-methoxyimino-2-(2-aminothiazol-4-yl)acetamido]-3-(3,3,3-trifluoropropenyl)-3-cephem-4-carboxylic acid (syn-isomer, trans-isomer) and its sodium salt.

8. A cephem compound which is selected from:
7-[2-methoxyimino-2-(2-aminothiazol-4-yl)acetamido]-3-(3,3,3-trifluoropropenyl)-3-cephem-4-carboxylic acid pivaloyloxymethyl ester (syn-isomer, cis-isomer) and its hydrochloride;
7-[2-methoxyimino-2-(2-aminothiazol-4-yl)acetamido]-3,(3,3,3-trifluoropropenyl)-3-cephem-4-carboxylic acid pivaloyloxymethyl ester (syn-isomer, trans-isomer) and its hydrochloride.

9. A cephem compound which is selected from:
7-[2-methoxyimino-2-(2-aminothiazol-4-yl)acetamido]-3-(3,3,3-trifluoropropenyl)-3-cephem-4-carboxylic acid 1-(ethoxycarbonyloxy) ethyl ester (syn-isomer, cis-isomer) and its hydrochloride;
7-[2-methoxyimino-2-(2-aminothiazol-4-yl)acetamido]-3,(3,3,3-trifluoropropenyl)-3-cephem-4-carboxylic acid 1-(ethoxycarbonyloxy) ethyl ester (syn-isomer, trans-isomer) and its hydrochloride.

10. A cephem compound which is selected from:
7-[2-methoxyimino-2-(2-aminothiazol-4-yl)acetamido]-3-(3,3,3-trifluoropropenyl)-3-cephem-4-carboxylic acid (5-methyl-2-oxo-1,3-dioxolen-4-yl)methyl ester (syn-isomer, cis-isomer) and its hydrochloride;
7-[2-methylimino-2-(2-aminothiazol-4-yl)acetamido]-3-(3,3,3-trifluoropropenyl)-3-cephem-4-carboxylic acid (5-methyl-2-oxo-1,3-dioxolen-4-yl)methyl ester (syn-isomer, trans-isomer) and its hydrochloride.

11. A pharmaceutical, antibacterial composition which comprises an antibacterially effective amount of the compound of the formula (I) as defined in claim 1 or a pharmaceutically acceptable salt or ester thereof, as the active ingredient, in combination with a pharmaceutically acceptable carrier for the active ingredient.

* * * * *